United States Patent
Sharp

[19]

[11] Patent Number: 6,120,453
[45] Date of Patent: Sep. 19, 2000

[54] THREE-DIMENSIONAL ULTRASOUND SYSTEM BASED ON THE COORDINATION OF MULTIPLE ULTRASONIC TRANSDUCERS

[76] Inventor: William A. Sharp, 42 Avon St., New Haven, Conn. 06511

[21] Appl. No.: 09/191,433

[22] Filed: Nov. 12, 1998

Related U.S. Application Data

[60] Provisional application No. 60/065,760, Nov. 17, 1997.

[51] Int. Cl.[7] .................................................. A61B 8/12
[52] U.S. Cl. ............................................. 600/463; 128/916
[58] Field of Search .................................... 600/437, 443, 600/447, 459, 462–463, 465–466; 128/916

[56] References Cited

U.S. PATENT DOCUMENTS

| | | |
|---|---|---|
| 4,798,210 | 1/1989 | Ledley . |
| 4,932,414 | 6/1990 | Coleman et al. . |
| 5,295,486 | 3/1994 | Wollschlager et al. . |
| 5,355,888 | 10/1994 | Kendall ................................... 600/443 |
| 5,396,890 | 3/1995 | Weng . |
| 5,398,691 | 3/1995 | Martin et al. ............................ 600/463 |
| 5,515,853 | 5/1996 | Smith et al. ............................. 128/916 |
| 5,515,856 | 5/1996 | Olstad et al. . |
| 5,546,949 | 8/1996 | Frazin et al. . |
| 5,673,697 | 10/1997 | Bryan et al. ............................ 600/443 |
| 5,724,978 | 3/1998 | Tenhoff ................................ 128/916 X |
| 5,957,844 | 9/1999 | Debel et al. ............................ 128/916 |

OTHER PUBLICATIONS

Marx, G., et al. Delineation of Site, Relative Size and Dynamic Geometry of Atrial Septal Defects by Real–Time Three–Dimensional Echocardiography pp. 482–490 Journal of the American College of Cardiology 1995: 25.

Belohlavek, M., et al. Three–and Four–Dimensional Cardiovascular Ultrasound Imaging: A New Era for Echocardiography pp. 221–240 Mayo Clinic Proceedings 1993: 68.

Mueller, G., et al. Three–Dimensional Ultrasound in the Evaluation of Fetal Head and Spine Anomalies pp. 372–378 Obstetrics & Gynecology 1996: 88.

*Primary Examiner*—Francis J. Jaworski
*Attorney, Agent, or Firm*—Douglas E. White

[57] ABSTRACT

Two or more ultrasound transducer probes applied to a body give information regarding the relative position of each by determining the time of transit of sound energy between each probe. Besides knowledge of the range from one probe to another, the orientation and bearing of one probe to the other is determined by calculating the relative direction by which sound energy arrives at a probe. By making the location of one of the probes be known through fixing it in space to a mechanical arm or similar mechanical device of knowable position, the absolute positions and orientations of both probes becomes known. Each of the two ultrasound probes may generate different views of the same structure. Such complimentary, and possibly simultaneous, views allow for greater precision and clearer three-dimensional images, as well as provide for more rapid accumulation of data. The primary application of this technology is to use an internal transesophageal and an external transabdominal probe to image the heart and nearby structures such as the aorta. However, this method could be applied to viewing any other area where ultrasound is able to be used to view that area from more than one location. One other example would be using one or more transabdominal probes as well as an intravaginal probe to create three-dimensional views of a fetus, the uterus and the ovaries.

20 Claims, 7 Drawing Sheets

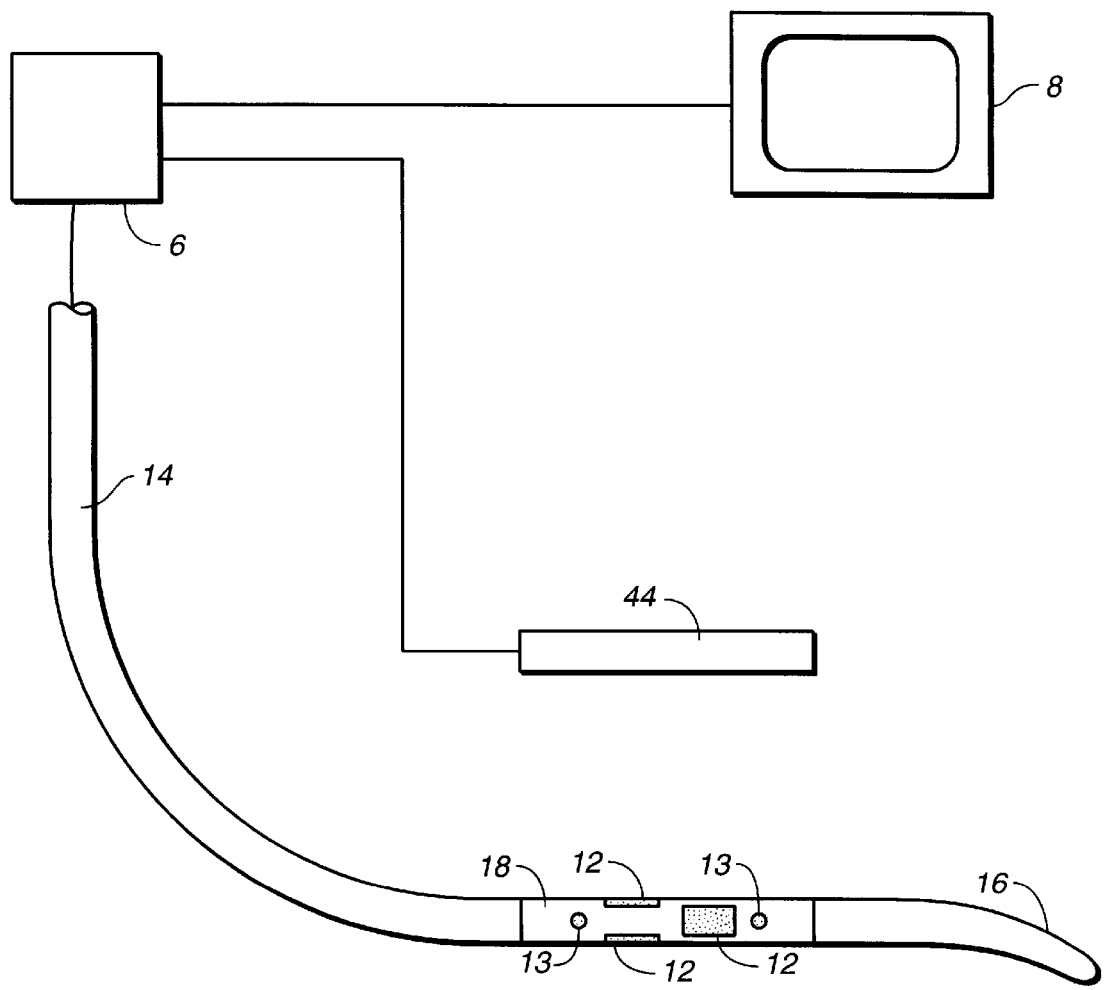
FIG._1
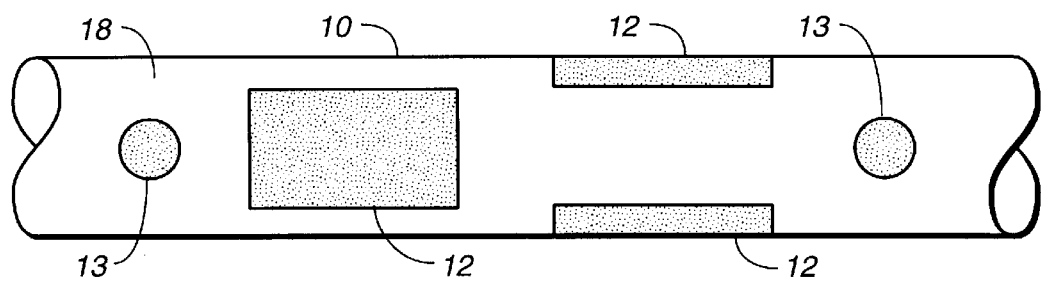
FIG._2

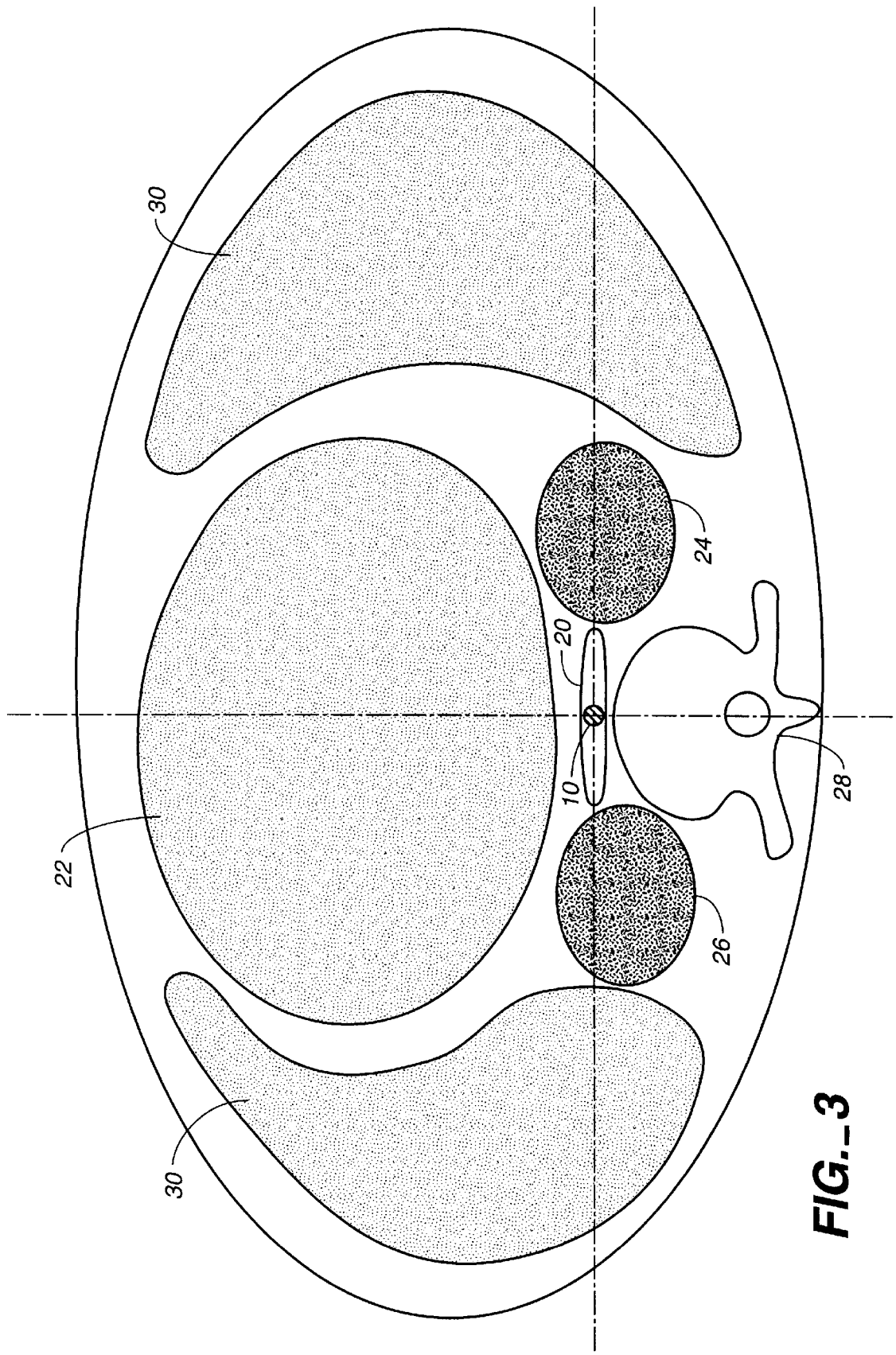
FIG._3

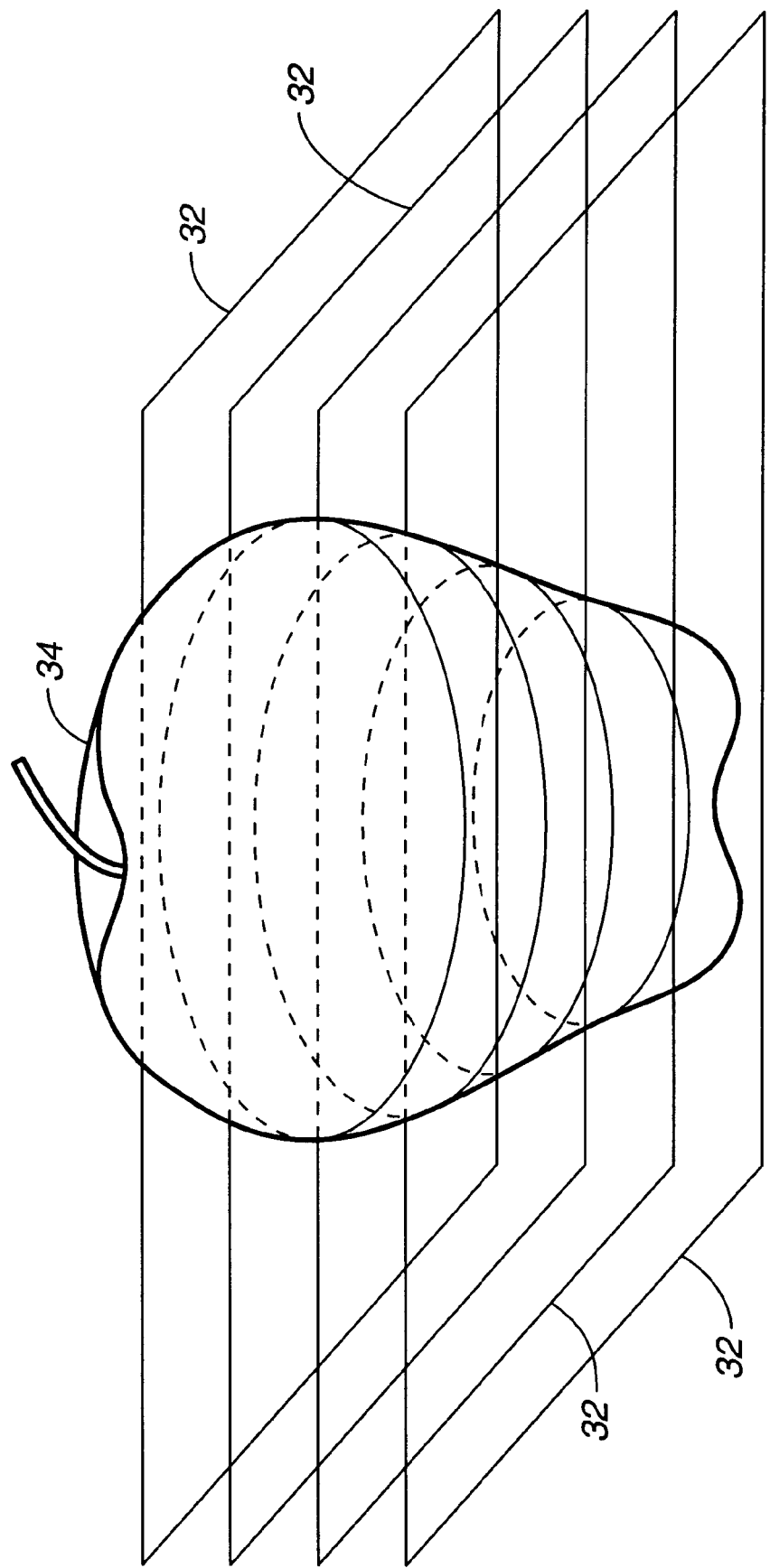
FIG._4

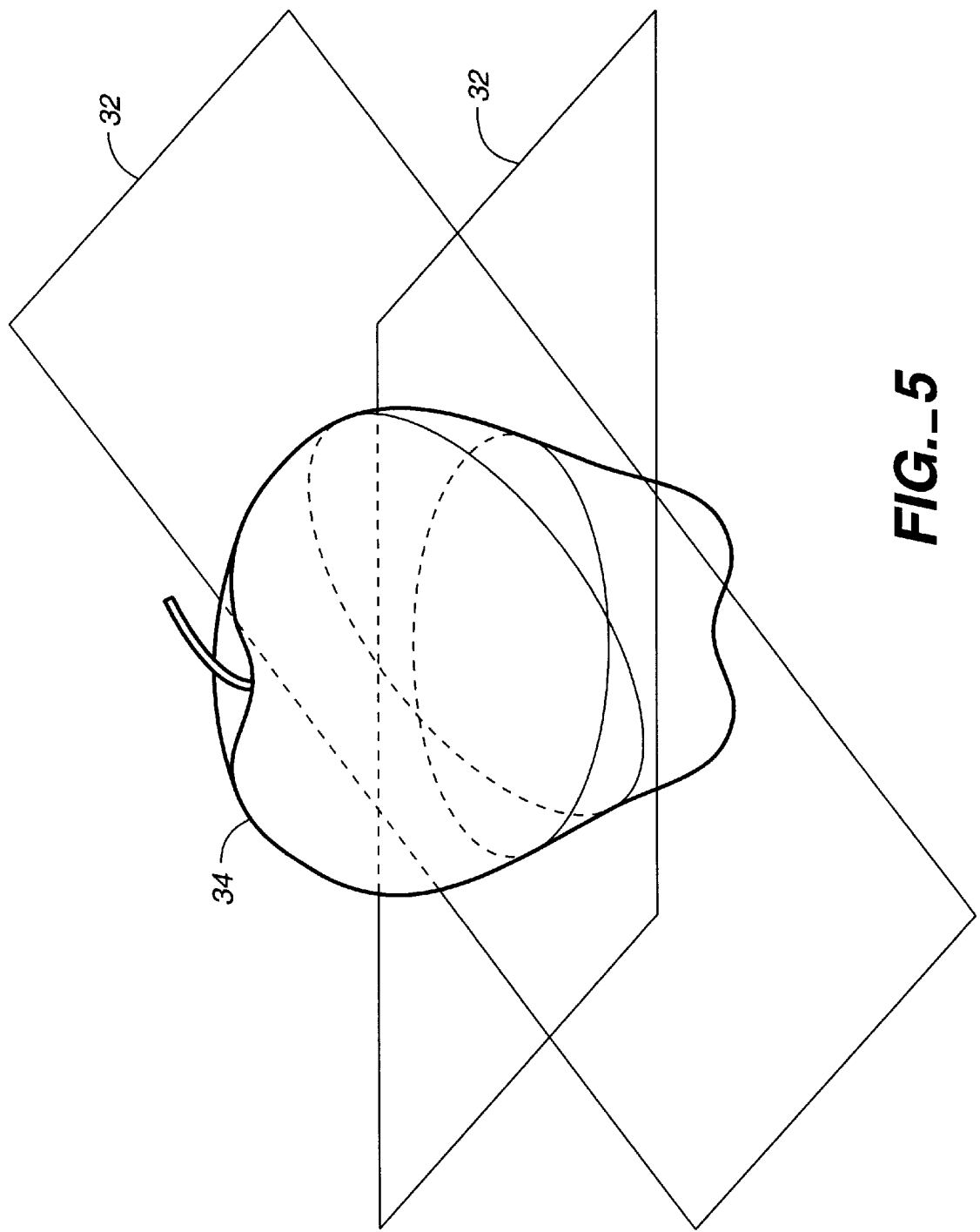
FIG._5

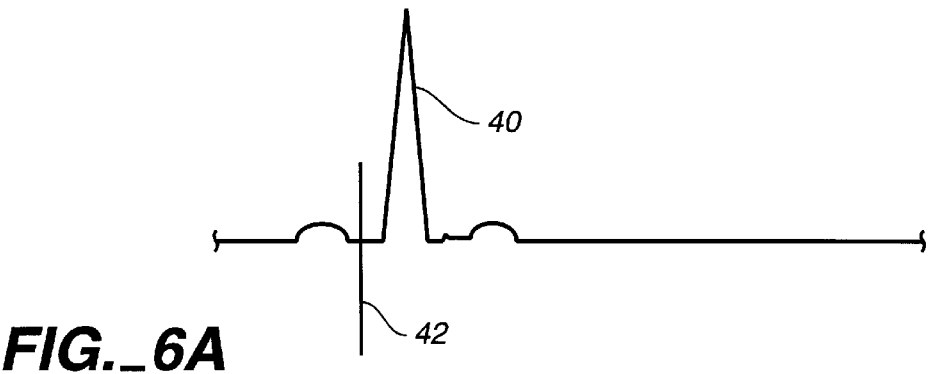
FIG._6A
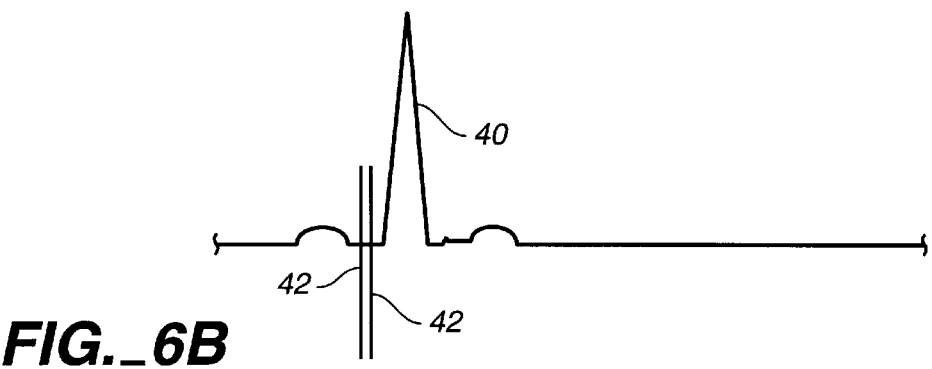
FIG._6B
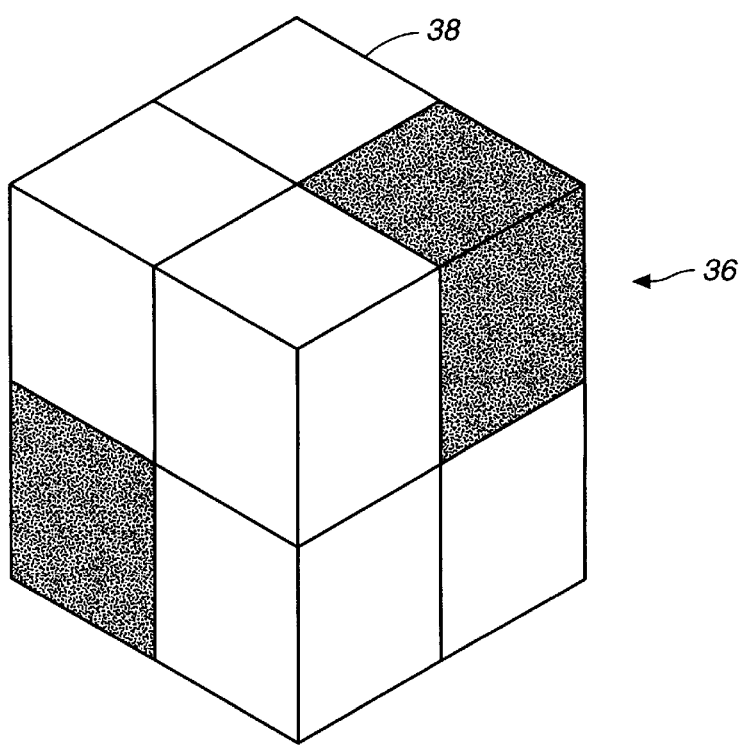
FIG._7

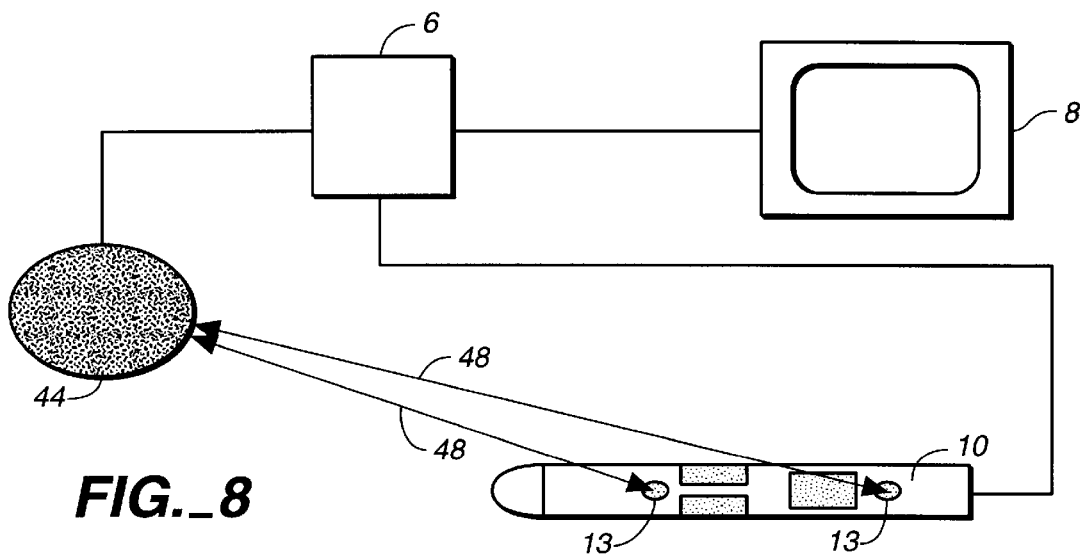
FIG._8
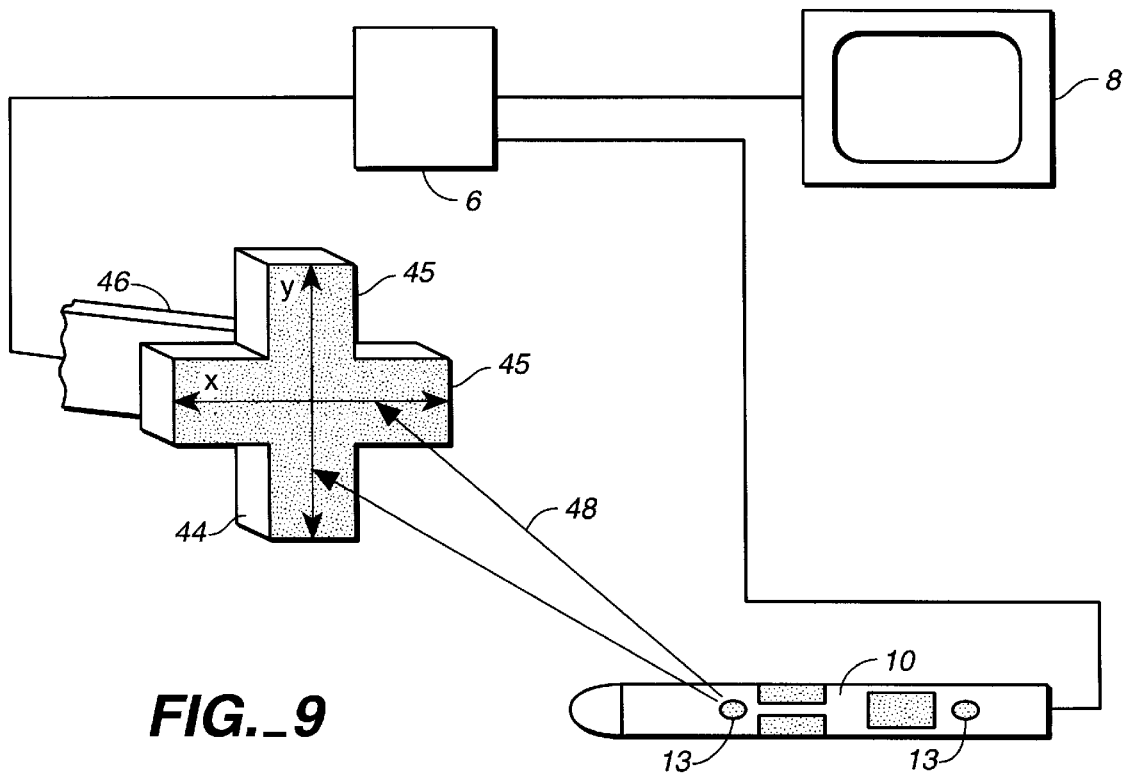
FIG._9

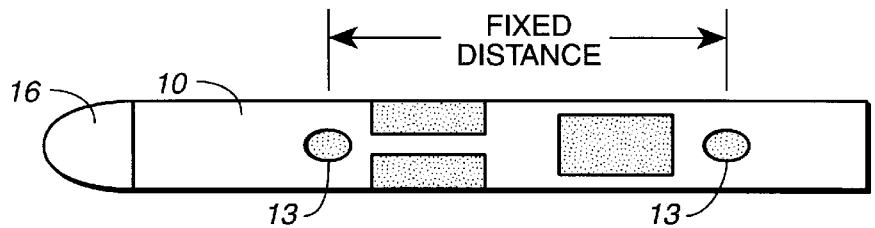
FIG._10
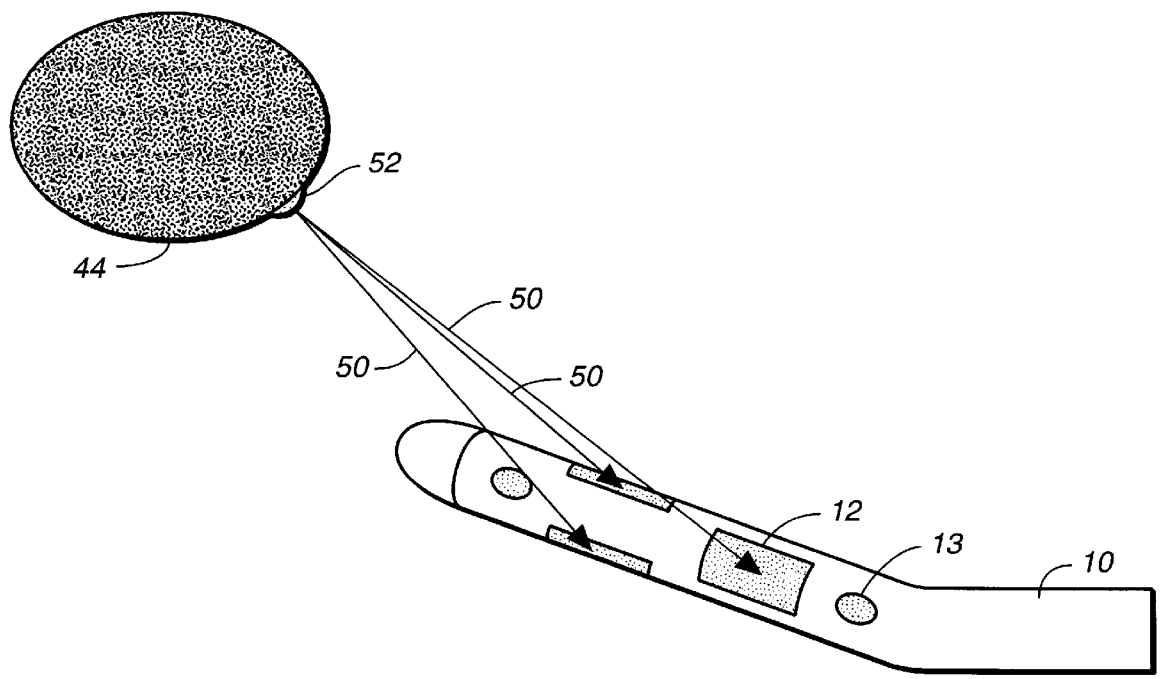
FIG._11

THREE-DIMENSIONAL ULTRASOUND SYSTEM BASED ON THE COORDINATION OF MULTIPLE ULTRASONIC TRANSDUCERS

CROSS REFERENCE TO RELATED APPLICATIONS

This application claims the benefit of U.S. Provisional Application No. 60/065,760, filed Nov. 17, 1997.

FEDERALLY SPONSORED RESEARCH OR DEVELOPMENT

Not applicable.

FIELD OF THE INVENTION

This invention relates to the use of ultrasound transducers to obtain three or four dimensional images of the heart and other internal human structures, more particularly to an apparatus and method which use two or more ultrasonic transducer probes acting in concert to produce and refine such images.

BACKGROUND OF THE INVENTION

Ultrasound technology in medicine continues to improve the ability of health care workers to obtain images of internal human structures. Not only are images obtained quickly, they also are delivered with minimal harm and discomfort to the patient. One current example of this technology is the real-time two-dimensional picture of the human fetus frequently obtained by expectant mothers when they get a sonogram by an obstetrician. These images are pie-shaped forms with the apex at the skin surface and showing ever deeper layers radiating out from the apex, namely, the wall of the uterus, the fetus, and then the opposite wall of the uterus. The depth of the image is limited by the frequency at which the sound is emitted, its amplitude and the currently available technology.

While visualizing the fetus may be the best known use of this technology in medicine, it is also used to look at the skin, the liver, the ovaries, the kidneys, and the heart. In looking at the heart it is invaluable because it provides a functional study. By this is meant that a real-time moving image of the heart (as it contracts in front of the observer) is obtained, yielding information about the contractions. This knowledge is readily obtained from watching the moving image on a computer monitor. Some examples of the interesting information that can be obtained are how much each chamber of the heart pumps with each beat, and what percentage of blood is expelled from each chamber with each contraction.

A simple explanation of ultrasound technology is as follows. An ultrasound transducer uses a piezoelectric crystal or similar device to convert electrical energy to sound vibrations and vice versa. High frequency sound energy is emitted by the transducer into a sound conductive medium. Since different structures in the human body conduct and reflect sound energy differently, the various times and intensity at which the sound wave energy is reflected and returned to the transducer can be used to reconstruct an image, using available computerized techniques. A simple analogy is the use of sonar to determine the range, bearing and size of a submarine located in the ocean. Sonar uses essentially the same principles of measuring reflected sound. In the study of the human body, the ranges to structures are much smaller, allowing hundreds of images to be obtained each second. This allows for the real-time visualization of moving structures.

The most commonly manifested use of ultrasound technology in medicine employs a phased array or other ultrasound transducer to obtain two-dimensional tomographic images of human structures. In other words, the images represent planar "slices" through the body. Different two-dimensional slices are obtained by adjusting the orientation and position of the transducer. An analogy would be the result obtained by a butcher when using a slicing machine to obtain thin sheets of ham. If the ham were rotated in the machine before each slice, different shaped slices could be obtained.

Following in this thought is the fact that if the sequence of the slices of ham are known, a reasonable approximation of the original ham can be obtained by restacking the original slices. A similar premise lies behind presently available three-dimensional ultrasound imaging, wherein a series of two-dimensional images of a structure in the human body is used to recreate pictorially a three-dimensional image of that structure. This is not a new idea, with several approaches currently being summarized in patents and the scientific literature. The basic premise of the current art is that if the time of imaging and the location of the ultrasound transducer are known, the order and position of individual two-dimensional slices is also known. A relatively simple computer algorithm then "stacks," or reassembles, these slices into a three-dimensional picture. The present application of this technology is limited by constraints in the accuracy of assumptions made about the position of the transducer as the individual two-dimensional images are taken. For example, it may be assumed that the position of the transducer is moving linearly, while, in fact, extraneous movements of the patient and the like may cause it to move non-linearly. Consequently, when the images are assembled ("stacked") according to such inaccurate positional assumptions, loss of focus and other image distortion results. In other cases, a constant velocity of movement is assumed, but this also is difficult to achieve in practice.

Sound waves are poorly transmitted by bone and air. This prevents adequate images from being obtained of, for example, the heart when attempting to look through ribs, the breastbone (sternum), or the lungs. In looking at the heart, there are two primary ways in which ultrasound beams can be directed. One way to avoid bone is by looking from the upper abdomen, just below the breastbone, and up at the heart. This is known as the transabdominal or subxiphoid view. The second way is by inserting a transducer probe into the esophagus—a structure which is in close proximity to the heart during much of its course from pharynx to stomach. This transesophageal view is widely regarded as allowing for superior ultrasound views of the heart. Different areas of the heart can be seen simply by sliding the transducer up and down in the esophagus. Obviously, this latter approach is less well tolerated by the patient, requiring sedation while the flexible probe (often 1 to 1.5 cm. in diameter) is manipulated in his or her esophagus. In addition, there are greater risks to the patient, including but not limited to, tears of the esophagus. The larger the probe and the longer it must remain in place, the greater are the discomfort and risks.

Prior developments in this field may be generally illustrated by reference to the following information disclosure statement:

U.S. PATENT DOCUMENTS

| U.S. Pat. No. | Patentee | Issue Date |
| --- | --- | --- |
| 5,546,949 | L. Frazin et al. | Aug. 20, 1996 |
| 4,932,414 | D. Coleman et al. | Jun. 12, 1990 |
| 5,398,691 | R. Martin et al. | Mar. 21, 1995 |
| 5,295,486 | H. Wollschlager et al. | Mar. 22, 1994 |
| 4,798,210 | R. Ledley | Jan. 17, 1989 |
| 5,515,856 | B. Olstad et al. | May 14, 1996 |
| 5,396,890 | L. Weng | Mar. 14, 1995 |

OTHER DOCUMENTS

Marx, G., et al., *Delineation of Site, Relative Size and Dynamic Geometry of Atrial Septal Defects by Real-Time Three-Dimensional Echocardiography*, Journal of the American College of Cardiology (1995: 25), pages 482–490.

Mueller, G., et al., *Three-Dimensional Ultrasound in the Evaluation of Fetal Head and Spine Anomalies*, Obstetrics & Gynecology (1996: 88), pages 372–378.

Belohlavek, M., et al., *Three- and Four-Dimensional Cardiovascular Ultrasound Imaging: A New Era for Echocardiography*, Mayo Clinic Proceedings (1993: 68), pages 221–240.

Returning to the currently used methods to create three-dimensional echocardiographic cardiographic images of the heart, the most successful systems use the transesophageal approach, employing different methods to determine the location of the transducer at the time each slice is obtained. One method, described by Martin et al. in the '691 patent above, uses an electromagnetic device to determine the intraesophageal position. An electromagnetic field is generated by a device placed outside, but near, the patient. A unit placed next to the ultrasound transducer within the probe creates a second electromagnetic field, allowing for a calculation of position of the probe relative to the electromagnetic device outside of the body. The transducer itself is attached to a mobile platform within the probe. This allows the probe to remain stationary while the rotating transducer obtains different image slices through the heart. These images are characterized by having planes that intersect along a common line.

A second method of three-dimensional echocardiography is described in the article by Marx et al. above. This method uses a probe which is attached to a stepper motor. The stepper motor advances the probe down the esophagus in predetermined increments. Once the probe is inserted in the esophagus, it is made rigid. As the probe is advanced, image slices are obtained whose planes are parallel to each other ("breadloaf" images), showing structures in the chest.

With these methods, and others, a scan data set is compiled for each image slice. As previously mentioned, two pieces of required information are the time of acquisition and the location of the probe in the body. Additional information includes the orientation of the probe and the time of acquisition in the cardiac cycle. This last piece of data accounts for the heart being a moving object undergoing contractions. Two ways in which this is done include linking the time of image acquisition to the corresponding time on the electronic signature of a heartbeat, namely the electrocardiogram, or linking each view to the heart sound being created at the moment of imaging. Both sound and electrocardiogram correlate well to the stage of contraction or relaxation of the beating heart. So, knowing all of this information, a computer reassembles a reproduction of a complete heartbeat in a three-dimensional representation.

The '949 patent to Frazin et al. describes the use of two ultrasound devices (one on an internal probe and one placed either externally or internally) to display on an ultrasound monitor the orientation and location of the internal probe. This patent teaches the use of dual ultrasound devices for guidance in moving and locating the internal probe, as opposed posed to the creation of accurate three-dimensional images.

Limitations of the present art include the need for inserting bulky apparatus in the patient's esophagus, which apparatus is used just for positioning the probe and maintaining its position. This apparatus can cause discomfort and injury to the patient, and its proper use may require great skill and an optimal environment. As noted above, inaccurate assumptions made about how such positional apparatus works, as well as unpredictable patient movement and other events that transpire during the procedure, tend to degrade the quality of the resultant image.

It therefore will be appreciated that there continues to be a need for a new and improved dynamic three-dimensional ultrasound imaging system which addresses the problems of construction, effectiveness and ease of use that are attendant in the prior art. In this respect, the present invention substantially fulfills this need.

SUMMARY OF THE INVENTION

There is need for an ultrasound imaging system which is superior to current ideas and devices regarding three-dimensional ultrasound, including but not limited to echocardiography, and which has all of the important advantages of the prior art, but which is faster, simpler, safer and capable of yielding greater and more accurate information. Accordingly, the apparatus and method described herein disclose the concept that two or more ultrasound probes applied to a body will give information regarding the relative position of each by determining the time of transit of sound energy between each probe. Besides knowledge of the range from one probe to another, the orientation and bearing of one probe to the other is determined by calculating the relative direction by which sound energy arrives at a probe. By making one of the probe's "absolute" location be known through fixing it in space to a mechanical arm or similar mechanical device of knowable position, the absolute positions and orientations of both probes become known. Thus, the absolute positions of scanned objects become known, enabling accurate three-dimensional reconstruction.

The second advantage of coordinating two ultrasound probes is that they each generate different views of the same structure. Such complimentary, and possibly simultaneous, views allow for greater precision and clearer three-dimensional images, as well as provide for more rapid accumulation of data. It is a relatively routine task for a computer to combine images from two or more sources in creating this better three-dimensional image. This programming is within the means of a programmer having ordinary skill in this art.

The primary application of this technology, as presently perceived, is to use an internal transesophageal and an external transabdominal probe to image the heart and nearby structures, such as the aorta, in dynamic three-dimensional cardiovascular ultrasonography. However, this method could be applied to viewing any other area of the body where ultrasound is able to be used to view that area from more than one location. One other example would be using one or more transabdominal probes as well as an intravaginal probe to create three-dimensional views of a fetus, the uterus and the ovaries. In other applications, the external probe might be placed in the transthoracic position.

Features and Advantages

An object of this invention is to teach an apparatus and method for ultrasound imaging which imparts greater precision and clarity to the images.

Another object is to provide such an apparatus and method which gathers a greater quantity of useful data during a particular period of time than do existing methods.

Yet another object is to provide such an ultrasound imaging system which is potentially less harmful and less discomforting to the patient and reduces or eliminates the need to sedate the patient.

Another object is to disclose means for obtaining more precise and varied quantified (non-visual) data than heretofore possible with two and three-dimensional ultrasound imaging systems.

Still another object is to provide a system which requires less skill, dexterity, and training to operate, so that it may be used by general health professionals and in emergency room situations—where the time to perform precise positioning of probes may not be available. The internal probe of this invention can be moved fairly randomly without the need for maintaining a fixed or stepped velocity. There is no need for the use of an optical endoscope for positioning.

Another object or advantage of this invention is that it can be used to provide real-time, or only marginally delayed, cinematic three-dimensional imaging ("four-dimensional" imaging). That is, it can be adapted to display the functions of an organ in simultaneous coordination with the actual functioning of said organ.

Still another object is to provide a device which may be left in place during treatment of a patient as a means of monitoring organ function and other structural functions over time. The device and method of this invention accomplishes this by requiring less precise probe positioning and by allowing smaller, less intrusive probes to be used. Furthermore, by providing monitoring in two planes, better extrapolation of the volume pumped in each heartbeat may be obtained.

Another feature is an apparatus that is suitable for production at relatively low cost.

Accordingly, an object is to disclose an ultrasound system for imaging an object including: a first probe having at least one first ultrasound transducer; a second probe having at least one second ultrasound transducer; and control unit means operably connected to at least said second probe for determining the position of one of said at least one first transducers of said first probe relative to the position of said second probe, and thereby the position of said object relative to the position of said second probe.

Another object is to disclose such apparatus further including combining means in said control unit means for combining two-dimensional ultrasound scan data into three-dimensional ultrasound scan data.

Yet another object or feature is said apparatus preferably further includes an ultrasound display operably connected to said control unit means.

Another feature is at least two first probe ultrasound beacon emitters spaced apart on said first probe.

Another feature is preferably there are four first probe scanning transducers on said first probe. Preferably, said first probe has a first probe beacon signal frequency and a first probe scanning frequency, said frequencies being different.

Still another feature is wherein said first probe is an internal probe of the transesophageal type and said second probe is an external probe.

A preferred feature disclosed herein is at least one second probe ultrasound beacon emitter on said second probe. Preferably, said second probe has a second probe beacon signal frequency equal to said first probe scanning frequency.

Another object is to disclose an ultrasound imaging system including: a first probe having a plurality of first probe ultrasound scanning transducers operating at a first frequency for producing two-dimensional ultrasound scan data, and at least two spaced-apart first probe ultrasound beacon emitters operating at a second frequency; a second probe having a second probe ultrasound transducer receiver operating at said second frequency and at least one second probe ultrasound beacon emitter operating at said first frequency; and an ultrasound control unit, said first and second probes electrically interconnected with said control unit.

Another object or feature is combining means in said control unit for combining two-dimensional ultrasound scan data into three-dimensional ultrasound scan data based upon positional data correlating a first probe position of said first probe relative to a second probe position of said second probe, said positional data obtained by sending second probe ultrasound signals at said first frequency from said second probe beacon emitter to said first probe and by sending first probe ultrasound signals at said second frequency from at least one first probe beacon emitter to said second probe.

A preferred feature is wherein said combining means correlates at least the range, bearing and orientation of said first probe relative to said second probe. Calculation of the rotation of the first probe may be said to be a feature of the combining means.

Other novel features which are characteristic of the invention, as to organization and method of operation, together with further objects and advantages thereof will be better understood from the following description considered in connection with the accompanying drawing, in which preferred embodiments of the invention are illustrated by way of example. It is to be expressly understood, however, that the drawing is for illustration and description only and is not intended as a definition of the limits of the invention. The various features of novelty which characterize the invention are pointed out with particularity in the claims annexed to and forming part of this disclosure. The invention resides not in any one of these features taken alone, but rather in the particular combination of all of its structures for the functions specified.

There has thus been broadly outlined the more important features of the invention in order that the detailed description thereof that follows may be better understood, and in order that the present contribution to the art may be better appreciated. There are, of course, additional features of the invention that will be described hereinafter and which will form additional subject matter of the claims appended hereto. Those skilled in the art will appreciate that the conception upon which this disclosure is based readily may be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract is neither intended to define the invention of this application, which is measured by the claims, nor is it intended to be limiting as to the scope of the invention in any way.

Certain terminology and derivations thereof may be used in the following description for convenience in reference only, and will not be limiting. For example, words such as "upward," "downward," "left," and "right" would refer to directions in the drawings to which reference is made unless otherwise stated. Similarly, words such as "inward" and "outward" would refer to directions toward and away from, respectively, the geometric center of a device or area and designated parts thereof. References in the singular tense include the plural, and vice versa, unless otherwise noted.

BRIEF DESCRIPTION OF THE DRAWING

The invention will be better understood and objects other than those set forth above will become apparent when consideration is given to the following detailed description thereof. Such description makes reference to the annexed drawing wherein:

FIG. 1 is a schematic elevation of a transesophageal transducer probe and associated ultrasound imaging apparatus for use in this invention;

FIG. 2 is a schematic broken sectional enlargement of the device of FIG. 1;

FIG. 3 is a schematic cross sectional plan view of the human chest, showing emplacement of the probe of FIG. 1;

FIG. 4 is a conceptual schematic illustrating the method of assembling a three-dimensional representation of an object using images taken through the object in parallel planes;

FIG. 5 is a conceptual schematic showing the method of FIG. 4 when the image planes are not parallel;

FIGS. 6A and 6B are graphic illustrations of an electrocardiogram;

FIG. 7 is a schematic perspective view of a data cube, showing illumination of pixels on, for example, a computer monitor;

FIG. 8 is a conceptual schematic showing how range from the internal probe of FIG. 1 to an external probe is determined in this invention;

FIG. 9 is a conceptual schematic showing how the bearing of a beacon emitter on the probe of FIG. 1 from an external probe is determined;

FIG. 10 is a conceptual schematic showing how the orientation of the probe of FIG. 1 relative to the external probe is determined; and FIG. 11 is a conceptual schematic showing how the rotation of the probe of FIG. 1 relative to the external probe is determined.

DRAWING REFERENCE NUMERALS 6 control unit
8 display
10 internal transesophageal probe
12 transducer
13 beacon emitter
14 ultrasonic catheter
16 catheter tip
18 rigid segment
20 esophagus
22 heart
24 aorta
26 vena cava
28 vertebral column
30 lungs
32 plane
34 apple
36 data cube
38 pixel
40 electrocardiogram
42 cycle position
44 external probe
45 receiver
46 mechanical arm
48 beacon from internal probe
50 beacon from external probe
52 beacon emitter

DETAILED DESCRIPTION OF THE INVENTION

This device uses multiple ultrasound probes (transducer-bearing devices), preferably two, to create images of structures inside the human body that are both three-dimensional and animated. Each ultrasound probe or device emits ultrasound beacon signals which are received by the other ultrasound device(s). This enables a central computerized control unit to calculate the relative positions of each probe at any time. Knowing the positions and orientations of the probes at any time, a series of two-dimensional images created with one or more individual probes is transformed into a three-dimensional representation of the structure in question. The image typically is displayed on a CRT, LCD or similar computer monitor or on a computer printout, or is stored in memory for later display. Using multiple probes aimed at each other and at the same structure allows for greater precision in configuring the three-dimensional image of the structure, thus providing for greater resolution and detail in the images.

While the concept described herein can be used to view many structures of the human body, or even non-biological structures, the following is a description of a preferred device which images the heart through a process called three-dimensional echocardiography.

Referring to FIGS. 1 and 2, there is illustrated therein an internal ultrasound device or transesophageal probe 10 on the end of an ultrasonic catheter 14, which generally cylindrical probe has one or more, preferably a plurality, of ultrasound transducers 12 arranged at convenient positions around its circumference near the catheter tip 16. The spatially fixed exterior probe 44 (FIGS. 8, 9 and 10) used in this invention, such as a transabdominal probe (only schematically illustrated), is of similar general construction, except that a lumen catheter and a flexible, anatomically conforming, catheter tip are not needed. Both probes are in electronic communication with the control unit means 6 and, preferably, with a CRT, LCD or similar display 8. The control unit 6 includes electronic circuit and computer program combining means for combining two-dimensional ultrasound scan data into three-dimensional ultrasound scan data based upon positional data correlating the position (range, bearing and orientation) of the internal transesophageal probe 10 relative to that of the external probe 44. Said data is obtained as described below.

A rigid segment 18 of the internal transesophageal probe 10, approximately 3.8 cm long, contains the plurality, preferably four, phased array (or equivalent) scanning ultrasonic transducers 12. The transducers can be separated by 90 degree arcs, or can be located in any other arrangement that allows 360 degree circumferential coverage around the probe 10. In addition to the four scanning transducers 12 located in the end of the probe are two ultrasound beacon emitters 13 producing a unique sound signature at a frequency different than the sound being used by the scanning transducers 12.

FIG. 3 is a schematic cross-section through a human chest which shows how such a transducer arrangement gives a full 360 degree view around the esophagus 20, showing not only the heart 22, but also the aorta 24, the vena cava 26, the vertebral column 28 and the lungs 30. The axes of FIG. 3 roughly demarcate the four zones covered by the four scanning transducers of the internal transesophageal probe 10.

Reconstructing a three-dimensional image is done with a sufficient number of two-dimensional images of a structure. FIG. 4 illustrates parallel two-dimensional planes 32 drawn through an apple 34. Should an apple be sliced in this manner with a knife, it would be relatively easy to restack the individual slices manually and thereby obtain a reasonable approximation of the intact apple. However, for accurate registration, the precise location of each slice with respect to adjacent slices must be known.

With the device described here, the analogous "slicing" (each two-dimensional image being a slice) of the heart is non-parallel, as the internal probe 10 sliding in the esophagus 20 does not follow a straight course. Returning to the apple analogy, FIG. 5 illustrates such random (non-parallel) planes intersecting an apple 34. If this were done with a knife, reconstructing the apple would be more difficult after the same number of slices. However, it is known to be only slightly more taxing for a computerized control unit to reconstruct a three-dimensional image from random plane ultrasound images, as long as the exact location and orientation of each plane 32 is known.

FIG. 7 illustrates a three-dimensional data cube 36 showing an arbitrary number of pixels 38 along each axis (in FIG. 7, four pixels 38 are shown for each of two two-dimensional planes). Since the two-dimensional images obtained from use of this invention already are in digital form, it is easy to assign them to a place on the three-dimensional cube 36, knowing the orientation of the cube with respect to the planes of the images. To create a moving three-dimensional image, an arbitrary number of data cubes is made each representing a discrete location in time in the electrocardiogram. Each data cube 36 is the compilation of all two-dimensional scan data obtained during a certain period of the electrocardiogram.

A cardiac cycle, which lasts approximately one second, is divided into preferably thirty fragments. Preferably, each ¹⁄₃₀th of a cardiac cycle is defined by certain well recognized positions 42 on the electrocardiogram 40, as illustrated in FIGS. 6A and 6B. A single heartbeat is represented by the electrocardiogram tracing 40 in FIGS. 6A and 6B. While sixteen frames per second is the approximate rate of ordinary consumer video, thirty frames per second yields a more fluid image for the purposes herein. However, in cases where thirty frames might require too much processing power, such as in full real time imaging, the electrocardiogram might be divided into larger intervals.

In this device, the moving image of the heart 22 is obtained from any number of cardiac cycles and the final moving image is an "averaged" three-dimensional image of the heart, the view being averaged over the amount of cardiac cycles it takes to acquire the data. It follows that the final image increases in resolution with the more slices obtained. An image obtained over, say, 15 seconds yields all the information needed. An "averaged" image over such a time span will be just as useful as a full image of the heart during one individual cardiac cycle—the useful information being cardiac output and other parameters of cardiac function.

In FIG. 6B, the two lines 42 represent how a reconstructed three-dimensional image would group together all two-dimensional images obtained during a certain span of the electrocardiogram. The span on the electrocardiogram could correlate to ¹⁄₁₆th to ¹⁄₄₀th of a second.

The most important aspect of this device then becomes apparent, namely, determining during three or four-dimensional imaging the orientation, position and rotation of a flexible probe at any moment within a biologic structure by means of the coordinated positional cross-referencing of at least a pair of ultrasound probes. The solution is as follows. Sound emitted within a biologic structure will travel across that structure (keeping distance and structures traversed the same) in a set amount of time. A beacon signal emitted at time X from one probe and received at time Y by another probe allows for a calculation of the distance between them, and other positional parameters, as these events are coordinated by a central computerized control unit 6.

FIG. 8 shows how the two beacons 48 from the emitters 13 in the internal probe 10 are received by the external probe 44, which allows the control unit 6 to perform a calculation of range from the external probe 44 to the beacon emitters on the internal probe 10. Both probes are in electronic communication with the control unit 6 and, preferably, a conventional ultrasound display 8. Sound energy emitted by beacon emitters 13 at preset times is received a certain time later by the external probe. This allows for a calculation of distance to each ultrasound beacon emitter.

FIG. 9 shows how the bearing from the external probe 44 to each beacon emitter 13 of the internal probe 10 is determined. The external probe 44 is attached to a mechanical arm 46 (both schematically illustrated in FIG. 9) and thus is spatially fixed with reference to the arm (said "arm" including any structure of known or readily ascertainable and trackable position). Slight patient motion is not an issue, as a spring mechanism keeps the transducer receiver 45 of the external probe 44 in contact with the skin surface in the event of patient activity. A relatively simple algorithm based on tracking the mechanical movement of the arm allows the computerized control unit 6 to calculate the "absolute" position of the external transabdominal probe's transducer at any particular time.

The construction of the external probe 44 allows it to passively receive sound energy in two planes (x and y) simultaneously. It is possible that this construction also allows imaging in two planes simultaneously. Sound beacon 48 emitted from a beacon 13 in the internal probe 10 is perceived as striking each point on each plane of the external probe at a specific discrete angle. Therefore, it is possible to determine the direction to each beacon emitter 13 from the external probe 44.

FIG. 10 illustrates the method in which the orientation of the internal probe 10 relative to the external probe 44 is determined. The beacon emitters 13 of the internal probe 10 are located in a rigid section of the otherwise flexible probe and thus are always a fixed distance apart. Knowing the range to each beacon emitter 13, knowing two planar coordinates to each emitter, and knowing the preset and fixed distance between each beacon emitter 13, a simple calculation allows for the determination of the attitude or orientation of the internal probe 10.

The rotation of the internal probe 10 is then calculated by the angle at which a beacon 50 from a beacon emitter 52 of the external probe 44 is received at the four transducer faces 12 in the internal probe. FIG. 11 shows this concept. Sound beacon 50 from the external probe strikes each of the four or more transducers 12 in the internal probe at a different angle. Already knowing range, bearing and orientation of the internal probe, it is now possible to determine the amount of rotation of the internal probe within, say, the esophagus.

It would not matter that the signal from the external probe 44 is not being emitted from a location perpendicular to the faces of the transducers 12 on the internal probe. Each phased array transducer 12 perceives it as arising from the plane in which it is focused. Each of the four or more transducers 12 receive the signal beacon 50 from the external probe 44 at a different angle and intensity. The computer control unit 6 (FIGS. 1, 8 and 9) already has calculated the orientation and distance to the internal probe 10. Simple trigonometry is then employed to calculate the rotation of the internal probe.

In this device, care is taken so that beacon signals 48 from the internal probe 10 are transmitted at frequencies that do not interfere with the ultrasound frequencies being used to obtain the two-dimensional images. It follows that the beacon signal 50 from the external probe 44 to assess rotation is emitted at the same frequency at which the internal transducers 12 are operating. The signal from the external probe to the internal probe is readily identified by the computer by its characteristic amplitude.

Sequencing of the signal emissions is important and easily done by the computerized control unit 6. For instance, the internal scanning transducers 12 can be functioning at all times. The signal 50 to determine rotation from the external probe 44 is also emitting continuously at a characteristic amplitude. However, the beacon emitters 13 on the internal probe intermittently produce signals 48 at the predetermined times so that the time to traverse to the external probe 44 can be measured. For the moment after the beacon emitters emitters 13 fire, the external probe's transducers are only in a listening mode, awaiting the arrival of the signal beacons 48 and subsequently allowing for a calculation of range and bearing to the beacon emitters 13 on the internal probe 10. The frequency of the signal beacons 48 are the same used by the optional scanning transducers of the external probe 44 in obtaining two-dimensional images. In between emissions from the internal probe beacon emitters 13, the external probe 44 preferably works to obtain its own two-dimensional images.

As noted, the external probe 44 has a transducer receiver 45 for the receiving beacon signals from the internal probe 10, and the external probe emits the signal 50 to allow for determination of internal probe rotation. In addition, the external probe apparatus 44 may have its own image scanning transducer or transducers (separate from or included within receiver 45—not separately illustrated), said scanning transducers acquiring images at a frequency different than the internal probe. In looking at the heart, these transabdominal views nicely complement those obtained from a transesophageal approach. These additional slices are applied to the data cubes 36, allowing for greater resolution in the final three-dimensional picture on the display 8. It follows that the data obtained from multiple perspectives are beneficial to achieving high final image clarity. The computer control unit 6 that is processing the data preferably works under commands only to use data points or pixels 38 seen in two different slices taken through the same point in space at the same time relative to the electrocardiogram 40. Any number of methods for processing the data could be devised, and are within the normal ability of the average computer programmer of ordinary skill practicing in this art.

In order to realize a three-dimensional picture of a beating heart 22 on the display 8, the liberal application of existing image recognition software is utilized. For instance, much of the information desired is simply of the heart 22 and aorta 24. Constructing these structures separated from the surrounding tissue such as lungs 30, veins 26 and breastbone ("segmentation") is not difficult. For example, human anatomy is reproducible enough such that a computer can be instructed, with some certainty, that a two-dimensional image obtained from point X at orientation Y, with Z rotation will most likely include cross sections through certain structures. These certain structures might include the left ventricle, the right ventricle and the descending aorta. In other words, using known relationships of anatomy, the computer is easily taught the probability of certain items at certain positions being certain structures. Such image recognition software is currently in use in many circumstances, for example, with known technology which automatically detects the border of the left ventricle, such as that available from the Hewlett Packard Co. of Palo Alto, Calif. Using this simplest anatomy recognition program readily allows for a three-dimensional construction of the inside of the left ventricle and the aorta. Even this application allows for the determination of left ventricular volume, and subsequently ejection fraction, cardiac output and rate of ventricular contraction. Applied to the aorta, disturbances to the interior lining such as in aortic dissection are readily seen.

As mentioned earlier, the principles of this invention can be applied to more than two probes. As long as one probe's position in space is "absolutely" known (i.e., is of fixed position with respect to the mechanical apparatus of the ultrasound imaging system) and the relative positions to other probes is then determined, the absolute position of all probes is known (and, from this, the absolute position of the viewed organ). Ultrasound signal beacons emanate from each of the non-fixed probes at predetermined times. This allows for a determination of range and bearing to each one. In this scenario, the data from three or more sets of two-dimensional images is incorporated in constructing one three-dimensional image.

Also, this invention is applicable to any other biologic (or non-biologic) application plication in which there is more than one acoustic window for looking at a structure. For instance, one acoustic probe could be placed intravaginally and the other extra-abdominally for acquiring three-dimensional views of a fetus or ovaries. This is one location where three or more probes could be used. Two could be placed on separate areas of the abdomen, while one is in the vagina.

In viewing the heart, the use of this invention is safer than current forms of transesophageal echocardiography. The internal probe 10 is of a smaller diameter than current versions and it may be inserted into the esophagus "blindly," not only because its small diameter construction and soft tip 16 are less likely to cause injury, but because its position is precisely followed through its communication with the external probe 44. In the case of prior art devices, a large diameter probe is needed—for example, to contain positioning and stepping mechanisms, as well as mechanisms to hold the probe fixedly within the esophagus 20.

The above disclosure is sufficient to enable one of ordinary skill in the art to practice the invention, and provides the best mode of practicing the invention presently contemplated by the inventor. While there is provided herein a full and complete disclosure of the preferred embodiments of this invention, various modifications, alternative constructions, and equivalents may be employed without departing from the true spirit and scope of the invention. Such changes might involve alternative materials, components, structural arrangements, sizes, operational features or the like.

For example, normally the frequencies of the beacons and the transducers of a single probe will be different, and these frequencies will have been cross-matched between probes to avoid interference, as discussed above. However, through appropriate timing and separation of consecutive signals, it may be possible for a transducer (or group of transducers) on one (or more) of the probes to operate both as a signal beacon and as a scanning transducer. As another example, the preferred internal probe has four phased array scanning transducers. A different number of ultrasound transducers of different type but similar function would be equivalent. Therefore, the above description and illustrations should not be construed as limiting the scope of the invention, which is defined by the appended claims.

What is claimed is:

1. An ultrasound system for imaging an object including:
  a first probe having at least one first ultrasound transducer for at least producing two-dimensional scan data of said object for imaging;
  a second probe having at least one second ultrasound transducer for receiving ultrasound signals from said first probe and for producing two-dimensional scan data of said object for imaging; and
  control unit means operably connected to at least said at least one second ultrasound transducer of said second probe for
    determining the position of said at least one first transducer of said first probe relative to the position of said at least one second ultrasound transducer of said second probe, and for
    determining, from said position of said at least one first transducer of said first probe relative to the position of said at least one second ultrasound transducer of said second probe, the position of said object relative to the position of said at least one second ultrasound transducer of said second probe.

2. The apparatus of claim 1 further including:
  combining means in said control unit means for combining said two-dimensional ultrasound scan data of said object into three-dimensional ultrasound scan data of said object by determining successive positions of said at least one first transducer of said first probe relative to the position of said at least one second ultrasound transducer of said second probe and by determining, from said successive positions of said at least one first transducer of said first probe relative to the position of said at least one second ultrasound transducer of said second probe, positions of alternate portions of said object relative to the position of said at least one second ultrasound transducer of said second probe.

3. The apparatus of claim 2 further including:
  an ultrasound display operably connected to said control unit means.

4. The apparatus of claim 2 wherein:
  said at least one first ultrasound transducer of said first probe includes at least two first probe ultrasound beacon emitters spaced apart on said first probe.

5. The apparatus of claim 4 wherein:
  said at least one first ultrasound transducer of said first probe includes four first probe scanning transducers on said first probe.

6. The apparatus of claim 5 wherein:
  said first probe ultrasound beacon emitters of said first probe have a first probe beacon signal frequency and said first probe scanning transducers of said first probe have a first probe scanning frequency, said frequencies being different.

7. The apparatus of claim 6 wherein:
  said first probe is an internal probe of the transesophageal type and
  said second probe is an external probe.

8. The apparatus of claim 6 wherein:
  said at least one second ultrasound transducer of said second probe includes at least one second probe ultrasound beacon emitter on said second probe.

9. The apparatus of claim 8 wherein: said at least one second probe ultrasound beacon emitter of said second probe has a second probe beacon signal frequency equal to said first probe scanning frequency.

10. An ultrasound imaging system including:
  a first probe having
    a plurality of first probe ultrasound scanning transducers operating at a first frequency for producing two-dimensional ultrasound scan data, and
    at least two spaced-apart first probe ultrasound beacon emitters operating at a second frequency;
  a second probe having
    a second probe ultrasound transducer receiver operating at said second frequency and
    at least one second probe ultrasound beacon emitter operating at said first frequency; and
  an ultrasound control unit, said first and second probes electrically interconnected with said control unit.

11. The apparatus of claim 10 further including:
  combining means in said control unit for combining two-dimensional ultrasound scan data into three-dimensional ultrasound scan data based upon positional data correlating a first probe position of said first probe relative to a second probe position of said second probe, said positional data obtained by sending second probe ultrasound signals at said first frequency from said second probe beacon emitter to said first probe and by sending first probe ultrasound signals at said second frequency from at least one first probe beacon emitter to said second probe.

12. The apparatus of claim 11 further including:
  an ultrasound display electrically interconnected with said control unit.

13. The apparatus of claim 12 wherein:
  said combining means correlates at least the range, bearing and orientation of said first probe relative to said second probe.

14. The apparatus of claim 13 further including:
a moveable mechanical arm, said second probe position fixed with respect to said mechanical arm.

15. The apparatus of claim 14 wherein:
said two-dimensional ultrasound scan data is produced by both probes.

16. A method of producing three or four-dimensional ultrasound images of a patient including the steps of:
providing a first probe having at least one first ultrasound transducer;
placing said first probe internal to said patient;
providing a second probe having at least one second ultrasound transducer;
placing said second probe external to said patient;
calculating the range, bearing and orientation of said first probe relative to said second probe by sending ultrasound signals between said two probes;
collecting first-probe two-dimensional scan data from said first probe;
collecting second-probe two-dimensional scan data from said second probe;
providing ultrasound control unit means; and
combining said first-probe two-dimensional scan data and said second-probe two-dimensional scan data into three-dimensional scan data with said control unit means.

17. The method of claim 16 further including the steps of:
providing an ultrasound display; and
displaying said three-dimensional scan data on said ultrasound display.

18. The method of claim 17 wherein:
in the step of placing said first probe, said first probe is placed in a transesophageal position;
in the step of placing said second probe, said second probe is placed in a transabdominal position; and
in the step of collecting two-dimensional scan data from at least said first probe, said scan data is collected from a heart and nearby structures of said patient.

19. The method of claim 17 further including the steps of:
providing a third probe having at least one third ultrasound transducer;
placing said third probe external or internal to said patient; and
collecting said two-dimensional scan data also from said third probe.

20. The method of claim 17 further including the step of:
collecting said two-dimensional scan data also from said second probe.

* * * * *